United States Patent
Doering et al.

(10) Patent No.: US 11,103,426 B2
(45) Date of Patent: Aug. 31, 2021

(54) ANHYDROUS, ANTIPERSPIRANT COMPOSITION HAVING IMPROVED STABILITY

(71) Applicant: Henkel AG & Co. KGaA, Duesseldorf (DE)

(72) Inventors: Thomas Doering, Dormagen (DE); Daniel Solich, Langenfeld (DE)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 0 days.

(21) Appl. No.: 16/224,279

(22) Filed: Dec. 18, 2018

(65) Prior Publication Data
US 2019/0183743 A1    Jun. 20, 2019

(30) Foreign Application Priority Data
Dec. 19, 2017   (DE) ..................... 10 2017 223 178.5

(51) Int. Cl.
| | | |
|---|---|---|
| *A61K 8/02* | (2006.01) | |
| *A61K 8/26* | (2006.01) | |
| *A61K 8/25* | (2006.01) | |
| *A61K 8/73* | (2006.01) | |
| *A61K 8/37* | (2006.01) | |
| *A61K 8/891* | (2006.01) | |
| *A61Q 15/00* | (2006.01) | |
| *A61K 8/58* | (2006.01) | |

(52) U.S. Cl.
CPC ............. *A61K 8/025* (2013.01); *A61K 8/25* (2013.01); *A61K 8/26* (2013.01); *A61K 8/37* (2013.01); *A61K 8/585* (2013.01); *A61K 8/732* (2013.01); *A61K 8/891* (2013.01); *A61Q 15/00* (2013.01); *A61K 2800/412* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 6,849,251 B2 | 2/2005 | Banowski et al. | |
| 2003/0108499 A1* | 6/2003 | Smith | A61K 8/044 424/65 |
| 2003/0185777 A1* | 10/2003 | Banowski | A61K 8/26 424/66 |
| 2010/0260698 A1 | 10/2010 | Galante et al. | |
| 2013/0280175 A1* | 10/2013 | Banowski | A61K 8/345 424/43 |
| 2017/0119653 A1 | 5/2017 | Doering et al. | |
| 2017/0196781 A1 | 7/2017 | Malle et al. | |

FOREIGN PATENT DOCUMENTS

| | | |
|---|---|---|
| DE | 10021056 A1 | 10/2001 |
| DE | 102017215011 A1 | 6/2018 |
| EP | 0570085 A2 | 11/1993 |
| FR | 3042972 A1 | 5/2017 |
| GB | 1549555 A | 8/1979 |
| GB | 2527044 A | 12/2015 |
| GB | 2560605 A | 9/2018 |
| WO | 0147476 A2 | 7/2001 |
| WO | 2010009977 A2 | 1/2010 |
| WO | 2010010510 A2 | 1/2010 |
| WO | 2016005250 A1 | 1/2016 |
| WO | 2016061440 A1 | 4/2016 |

OTHER PUBLICATIONS

Agrana Starch product page (2014).*
SPX Antiperspirants Process Bulletin (archived from Jun. 24, 2016 and obtained from <https://web.archive.org/web/20160624133413/https://www.spxflow.com/en/assets/pdf/PB-Antiperspirants_3041_US_tcm11-7620.pdf>.*

* cited by examiner

*Primary Examiner* — Patricia Duffy
*Assistant Examiner* — Garen Gotfredson
(74) *Attorney, Agent, or Firm* — Lorenz & Kopf, LLP

(57) ABSTRACT

The subject of the present application is an antiperspirant composition for personal body care having improved stability of the suspension contained, which contains a mixture of at least one oil, rice starch, at least one hydrophobically modified clay mineral and an antiperspirant active substance in the form of spherical particles.

6 Claims, No Drawings

ANHYDROUS, ANTIPERSPIRANT COMPOSITION HAVING IMPROVED STABILITY

CROSS-REFERENCE TO RELATED APPLICATION

This application claims priority to German Patent Application No. 10 2017 223 178.5, filed Dec. 19, 2017, which is incorporated herein by reference in its entirety.

TECHNICAL FIELD

The present disclosure relates to substantially anhydrous, antiperspirant compositions which have improved stability with respect to the suspensions of the antiperspirant active substances used in oil, a non-therapeutic method for reducing and/or regulating perspiration and/or body odor, and the use of certain types of starch and minerals to improve the stability of suspensions of antiperspirant active substances.

BACKGROUND

Commercially available antiperspirant compositions, also referred to below as antiperspirants, contain at least one water-soluble astringent inorganic or organic salt of aluminum as an antiperspirant active substance. The antiperspirant active substances have no direct influence on the activity of the sweat glands, but rather minimize sweat secretion by narrowing the outflow channels. The Al salts in this case cause sweat inhibition on the treated skin surfaces through superficial blockage of the sweat gland ducts as a result of Al-mucopolysaccharide precipitation. Antiperspirant compositions are usually applied in the armpit area.

Antiperspirant compositions are available in a variety of dosage forms, for example, as a sprayable composition having a propellant. Such compositions are usually filled in spray cans of aluminum or (more rarely) tinplate, which are protected against corrosion by an interior coating. Corrosion damage may occur, however, despite such a protective coating. A further problem with such products is that the valve clogs. A corrosion inhibiting and/or valve clogging reducing composition would therefore be desirable for these special dosage forms.

Sprayable compositions having propellant are usually based on suspensions of astringent salts such as aluminum chlorohydrate (ACH) in non-polar oils such as cyclomethicones. These suspensions must be stable for as long as possible. When the salt particles sediment before or during filling, deviations in the composition occur. When the salt particles sediment after filling, the effect may be that when the spray can is insufficiently shaken for a time, the antiperspirant composition sprayed by the consumer is uneven and has a poor antiperspirant effect. For formulations with unmilled and therefore spherical ACH particles, this poses a particular challenge because the round particles sediment more easily than the milled particles having an irregular surface.

There is therefore a continuing need for antiperspirant compositions which remain stable for a long time and do not sediment.

BRIEF SUMMARY

This disclosure provides an antiperspirant composition for personal body care that includes:

a) at least one antiperspirant active substance present in the form of spherical particles, in suspended, undissolved form, and selected from aluminum salts, in a total amount of about 5 to about 40% by weight,
b) about 0.1 to about 10% by weight of rice starch,
c) about 0.1 to about 10% by weight of hydrophobically modified clay mineral,
d) at least one oil in a total amount of about 20 to about 94.8% by weight,
wherein all weight % specifications are based on the weight of the composition, without taking into account any propellants which may be present.

This disclosure also provides a non-therapeutic, cosmetic method for reducing and/or regulating perspiration and/or body odor, in which the aforementioned composition is applied in an effective amount to the skin.

This disclosure still further provides a sprayable antiperspirant including the aforementioned composition present in an aerosol can with a compressed gaseous propellant.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

An object of the present disclosure was to provide antiperspirant compositions which form as stable as possible suspensions of powdery antiperspirant active substances, in particular aluminum chlorohydrate, in non-polar oils.

Surprisingly, it has been found that the object is achieved by antiperspirant active substances, in particular aluminum chlorohydrate, in the form of spherical particles in combination with rice starch and hydrophobically modified clay minerals, while no such pronounced stabilization is achieved with other types of starch.

A subject of the present disclosure is therefore a substantially anhydrous, antiperspirant composition for personal body care containing a) at least one antiperspirant active substance present in the form of spherical particles, in suspended, undissolved form, and selected from aluminum salts, in particular aluminum chlorohydrate, in a total amount of from about 5 to about 40% by weight, preferably from about 10 to about 35% by weight, especially preferably from about 15 to about 28% by weight, most preferably from about 23 to about 27% by weight,
b) from about 0.1 to about 10% by weight, preferably from about 0.4 to about 2% by weight of rice starch,
c) from about 0.1 to about 10% by weight, preferably from about 1.5 to about 3.5% by weight of hydrophobically modified clay mineral,
d) at least one oil in a total amount of from about 20 to about 94.8% by weight, preferably from about 40 to about 85% by weight, more preferably from about 50 to about 80% by weight, most preferably from about 60 to about 75% by weight, wherein all weight % specifications are based on the weight of the composition, without taking into account any propellants which may be present.

"Normal conditions" in the context of the present application are a temperature of 20° C. and a pressure of about 1013.25 mbar. Melting point specifications also refer to a pressure of about 1013.25 mbar.

Unless stated otherwise, all amount specifications are based on the total weight of the antiperspirant composition as contemplated herein. Any added propellants are not included in the antiperspirant composition of the present disclosure, therefore, all amount specifications are based on the total weight of the propellant-free antiperspirant composition, unless otherwise specified.

"Substantially anhydrous" means, as contemplated herein, a content of free water of not more than about 7% by weight, based on the total composition.

"Free water" in the context of the present application is water that is not present in the form of water of crystallization, water of hydration or similar molecularly bound water in the antiperspirant composition. The content of water of crystallization, water of hydration or similar molecularly bound water which is present in the constituents used, in particular in the antiperspirant active substances, does not constitute free water in the context of the present application. Free water is, for example, water which is added to the composition as contemplated herein as a solvent, as a gel activator or as a solvent constituent of other active substances.

The antiperspirant compositions as contemplated herein contain, based on their total weight, about 0 to about 7% by weight free water. As contemplated herein, preferred antiperspirant compositions contain, based on their total weight, about 0 to about 6% by weight of free water, preferably about 0 to about 5% by weight, particularly preferably about 0 to about 4% by weight, most preferably about 0 to about 3% by weight of free water. The antiperspirant compositions as contemplated herein are thus to be regarded as substantially anhydrous.

The compositions as contemplated herein contain, based in each case on their weight, from about 0.1 to about 10% by weight, preferably from about 0.4 to about 2% by weight, of rice starch.

The rice starch used as contemplated herein is obtained from rice. In preferred compositions as contemplated herein, the rice starch includes from about 10 to about 40% by weight, preferably from about 20 to about 30% by weight, particularly preferably from about 22 to about 28% by weight of amylose and from about 60 to about 90% by weight, preferably from about 70 to about 80% by weight, more preferably from about 72 to about 78% by weight of amylopectin, based on the weight of the rice starch.

Compositions as contemplated herein contain rice starch in a total amount of from about 0.1 to about 5% by weight, preferably from about 0.2 to about 2% by weight, particularly preferably from about 0.4 to about 1% by weight, based on the weight of the composition, preferably as a powder treated with cationic surfactant, more preferably with a fraction of the cationic surfactant content of from about 0.01 to about 3% by weight, most preferably from about 0.1 to about 0.15% by weight, based on the weight of the rice starch.

Preferred cationic surfactants are alkyltrimethylammonium chlorides, more preferably $C_{12}$-$C_{22}$ alkyltrimethylammonium chlorides, preferably $C_{16}$ alkyltrimethylammonium chloride (cetrimonium chloride).

The compositions as contemplated herein contain at least one hydrophobically modified clay mineral. Preferred hydrophobically modified clay minerals are selected from hydrophobically modified montmorillonites, hydrophobically modified hectorites and hydrophobically modified bentonites, more preferably disteardimonium hectorites, stearalkonium hectorites, quaternium-18 hectorites and quaternium-18 bentonites. Preferred compositions as contemplated herein are exemplified in that they contain at least one hydrophobically modified clay mineral in a total amount of from about 0.1 to about 10% by weight, preferably from about 1 to about 7% by weight, particularly preferably from about 1.5 to about 6% by weight, very preferably from about 1.5 to about 3.5% by weight, each based on the total weight of the propellant-free composition as contemplated herein.

Hydrophobically modified clay minerals are understood to mean clay minerals whose naturally occurring metal cations are wholly or partially replaced by cations substituted with hydrophobic groups, preferably ammonium cations substituted by long-chain alkyl groups, wherein the long-chain alkyl groups contain preferably about 5 to about 30, more preferably about 7 to about 25, most preferably about 10 to about 20 carbon atoms.

The compositions as contemplated herein contain at least one antiperspirant active substance that is selected from aluminum salts. Preferred antiperspirant active substances are selected from the water-soluble astringent inorganic and organic salts of aluminum.

As contemplated herein, water solubility is understood to mean a solubility of at least about 3% by weight at about 20° C., that is, amounts of at least about 3 g of the antiperspirant active substance are soluble in about 97 g of water at about 20° C. As contemplated herein, water solubility is understood to mean a solubility of at least about 5% by weight at about 20° C., that is, amounts of at least about 5 g of the antiperspirant active substance are soluble in about 95 g of water at about 20° C.

Particularly preferred antiperspirant active substances are selected from aluminum chlorohydrate, in particular aluminum chlorohydrate having the general formula $[Al_2(OH)_5Cl.1$-$6H_2O]_n$, preferably $[Al_2(OH)_5Cl.2$-$3H_2O]_n$, which can be present in non-activated or in activated (depolymerized) form, and aluminum chlorohydrate having the general formula $[Al_2(OH)_4Cl_2.1$-$6H_2O]_n$, preferably $[Al_2(OH)_4Cl_2 2$-$3H_2O]_n$, which may be in non-activated or in activated (depolymerized) form.

In the compositions as contemplated herein, the antiperspirant active substance, preferably aluminum chlorohydrate, is present in the form of spherical particles. The term "spherical particles" is understood to mean particles which are ellipsoidal, preferably ellipsoidal, with at least two axes of the same length, and which are extremely preferably spherical. The axial lengths of an ellipsoidal particle differ by at most about 30%, preferably by at most about 20%, more preferably by at most about 10%, most preferably by at most about 3% from each other, based on the length of the longest axis.

"Ellipsoid-shaped" and "spherical" mean that the particles appear as ellipsoids or spheres when viewed under a microscope at about a thousand times magnification. Ellipsoidal or spherical does not necessarily mean that the particles have a perfectly smooth surface.

In compositions as contemplated herein, preferably from about 70 to about 95% by weight of the particles have a size of more than about 10 μm, from about 80 to about 100% by weight of the particles have a size of up to about 75 μm and from about 90 to about 100% by weight of the particles have a size of up to about 125 μm, and most preferably from about 75 to about 80% by weight of the particles have a size greater than about 10 μm, from about 90 to about 100% by weight of the particles have a size of up to about 75 μm and from about 99 to about 100% by weight of the particles have a size of up to about 125 μm, in each case on the weight of the antiperspirant active substance. "Size" is understood to mean the diameter in the case of spherical particles and the length of at least two axes in the case of ellipsoidal particles. As contemplated herein, the spherical particles are preferably unmilled.

Also preferred are aluminum sesquichlorohydrate, aluminum dichlorohydrate, aluminum chlorohydrex-propylene glycol (PG) or aluminum chlorohydrex-polyethylene glycol (PEG), aluminum sesquichlorohydrex PG or aluminum sesquichlorohydrex PEG, aluminum PG-dichlorhydrex or aluminum PEG-dichlorhydrex, aluminum hydroxide, potassium aluminum sulfate ($KAl(SO_4)_2$ $12H_2O$, alum), dehydrated alum ($KAl(SO_4)_2$ with zero to 11 moles of water of crystallization), sodium aluminum chlorhydroxactate, aluminum bromohydrate, aluminum chloride, aluminum sulfate, aluminum lactate, sodium aluminum chlorohydroxylactate. Particularly preferred antiperspirant active substances as contemplated herein are selected from so-called "activated" aluminum salts, which are also referred to as "antiperspirant active substances" with "enhanced activity". Such active substances are known in the art and are also commercially available. Activated aluminum salts are usually produced by heat treating a relatively dilute solution of the salt (for example, about 10% by weight of salt) to increase its HPLC peak from about 4 to about peak 3 area ratio. The activated salt can then be dried to a powder, in particular spray-dried. In addition to spray drying, for example, drum drying is also suitable.

Activated aluminum salts typically have an HPLC peak 4-to-peak 3 area ratio of at least about 0.4, preferably at least about 0.7, more preferably at least about 0.9, wherein at least about 70% of the aluminum is attributed to these peaks.

Further preferred antiperspirant active substances are basic calcium aluminum salts. These salts are prepared by reacting calcium carbonate with aluminum chlorhydroxide or aluminum chloride and aluminum powder or by adding calcium chloride dihydrate to aluminum chlorhydroxide.

Further preferred activated aluminum salts are those of the general formula $Al_2(OH)_{6-a}X_a$, wherein X is Cl, Br, I or $NO_3$ and "a" is a value of about 0.3 to about 5, preferably from about 0.8 to about 2.5 and particularly preferably about 1 to about 2, so that the molar ratio of Al:X is 0.9:1 to 2.1:1, as disclosed, for example, in U.S. Pat. No. 6,074,632. In general, some water of hydration is associatively bound to these salts, typically about 1 to about 6 moles of water per mole of salt. Particularly preferred is aluminum chlorohydrate (that is, X is Cl in the aforementioned formula) and especially 5/6 basic aluminum chlorohydrate wherein "a" is about 1 so that the molar ratio of aluminum to chlorine is 1.9:1 to 2.1:1. Zirconium-free aluminum sesquichlorohydrates particularly preferred as contemplated herein have a molar metal-to-chloride ratio of about 1.5:about 1 to about 1.8:about 1.

Particularly preferred compositions as contemplated herein are exemplified in that the at least one antiperspirant active substance is present in a total amount of from about 5 to about 40% by weight, preferably about 10 to about 35% by weight, more preferably from about 15 to about 28% by weight and most preferably from about 23 to about 27% by weight, based on the total weight of the composition, without taking into account possibly existing propellant.

As further ingredients, the compositions as contemplated herein contain at least one oil which is liquid under normal conditions, which oil constitutes a carrier fluid or a suspension medium for the at least one antiperspirant active substance.

In the case of cosmetic oils, a distinction is made between volatile and non-volatile oils. Non-volatile oils are understood to mean oils which have a vapor pressure of less than about 2.66 Pa (about 0.02 mm Hg) at about 20° C. and an ambient pressure of about 1013 hPa. Volatile oils are understood to mean those oils which, at about 20° C. and an ambient pressure of about 1013 hPa, have a vapor pressure of about 2.66 Pa to about 40,000 Pa (about 0.02 mm to about 300 mm Hg), preferably about 12 to about 12,000 Pa (about 0.1 to about 90 mm Hg), more preferably about 13 to about 8,000 Pa, exceptionally preferably about 30 to about 3,000 Pa, further preferably about 100 to about 400 Pa.

The at least one oil is preferably selected from volatile or nonvolatile silicone oils; esters of linear or branched saturated or unsaturated fatty alcohols having from about 2 to about 30 carbon atoms with linear or branched saturated or unsaturated fatty acids having from about 2 to about 30 carbon atoms which may be hydroxylated; dicarboxylic acid esters of linear or branched $C_2$-$C_{10}$ alkanols; benzoic acid esters of linear or branched $C_{8-22}$ alkanols; mono- and polyesters of lactic acid, citric acid, tartaric acid or adipic acid with a monohydric alcohol having about 2 to about 9 carbon atoms; mono- and polyesters of lactic acid, citric acid, tartaric acid or adipic acid with a di-, tri- or tetravalent alcohol having about 2 to about 9 carbon atoms; symmetric, unsymmetrical or cyclic esters of carbonic acid with fatty alcohols; $C_5$-$C_{30}$ isoparaffins; and branched saturated or unsaturated fatty alcohols having about 6 to about 30 carbon atoms The at least one oil is present in a total amount of to about 20 to about 94.8% by weight, preferably to about 40 to about 85% by weight, more preferably to about 50 to about 80% by weight, most preferably to about 60 to about 75% by weight in the composition, based on the weight of the composition, without taking into account possibly existing propellant.

Preferred volatile silicone oils are selected from dialkyl and alkylaryl siloxanes which have a vapor pressure of less than about 2.66 Pa (about 0.02 mm Hg) at about 20° C. and an ambient pressure of about 1013 hPa, such as octamethylcyclotetrasiloxane, decamethylcyclopentasiloxane, dodecamethylcyclohexasiloxane, dimethylpolysiloxane, low molecular weight phenyl trimethicone and methylphenylpolysiloxane, but also hexamethyldisiloxane, octamethyltrisiloxane and decamethyltetrasiloxane. Particular preference is given to volatile silicone oils which are cyclic, such as octamethylcyclotetrasiloxane, decamethylcyclopentasiloxane and dodecamethylcyclohexasiloxane and mixtures thereof, as described, for example, in the commercial products DC 244, 245, 344 and 345 from Dow Corning (vapor pressure about 13-15 Pa at 20° C.), decamethylcyclopentasiloxane is exceptionally preferred.

Likewise particularly preferred are volatile linear silicone oils having about 2 to about 10 siloxane units, in particular hexamethyldisiloxane ($L_2$), octamethyltrisiloxane ($L_3$), decamethyltetrasiloxane ($L_4$) and any mixtures of two and three of $L_2$, $L_3$ and/or $L_4$, preferably such mixtures as present, for example, in the commercial products DC 2-1184, Dow Corning® 200 (about 0.65 cSt) and Dow Corning® 200 (1.5 cSt) from Dow Corning. A further preferred volatile silicone oil is a low molecular weight phenyl trimethicone having a vapor pressure of about 2000 Pa at about 20° C. as available, for example, from GE Bayer Silicones/Momentive under the name Baysilone Fluid PD 5.

Volatile silicone oils are excellently suitable carrier oils for antiperspirant compositions as contemplated herein, since they give them a pleasant feeling on the skin and little textile soiling.

Preferred nonvolatile silicone oils are selected from linear polydimethylsiloxanes having kinematic viscosities (about 25° C.) in the range from about 5 to about 350 cSt, preferably about 5 to about 100 cSt or also about 10 to about 50 cSt.

Preferred esters of linear or branched saturated or unsaturated fatty alcohols having about 2 to about 30 carbon atoms with linear or branched saturated or unsaturated fatty acids having about 2 to about 30 carbon atoms, which may be hydroxylated, are preferably selected from isopropyl palmitate, isopropyl stearate, isopropyl myristate, 2-ethylhexyl palmitate, 2-ethylhexyl stearate, 2-hexyldecyl stearate, 2-hexyldecyl laurate, isononyl isononanoate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyloctanoate, diisotridecylacetate, n-hexyl laurate, n-decyl oleate, oleyl oleate, oleyl erucate, erucyl oleate and erucyl erucate and mixtures of the aforementioned esters, more preferably from isopropyl palmitate, isopropyl stearate, isopropyl myristate, 2-ethylhexyl palmitate and 2-ethylhexyl stearate.

Preferred dicarboxylic acid esters of linear or branched $C_2$-$C_{10}$ alkanols are selected from diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate and mixtures of the aforementioned esters.

Preferred benzoic acid esters of linear or branched $C_{8-22}$ alkanols are selected from dodecyl benzoate, tridecyl benzoate, tetradecyl benzoate, pentadecyl benzoate, hexadecyl benzoate, octadecyl benzoate, 2-methylheptadecyl benzoate, octyl dodecyl benzoate. Particular preference is given to benzoic acid C12-C15 alkyl esters, for example, available as a commercial product Finsolv® TN, benzoic acid isostearyl ester, 2-ethylhexyl benzoate, and benzoic acid 2-octyldocecyl ester, wherein benzoic acid C12-C15 alkyl esters are highly preferred.

Triethyl citrate is preferred among the mono- and polyesters of lactic acid, citric acid, tartaric acid or adipic acid with a monohydric alcohol having about 2 to about 9 carbon atoms.

Triglyceride oils of linear or branched, saturated or unsaturated, optionally hydroxylated $C_{8-30}$ fatty acids, in particular natural oils, e.g., soybean oil, cottonseed oil, sunflower oil, palm oil, palm kernel oil, linseed oil, almond oil, castor oil, corn oil, rapeseed oil, olive oil, sesame oil, thistle oil, wheat germ oil, peach kernel oil and the liquid fractions of coconut oil and the like, but also synthetic triglyceride oils, in particular capric/caprylic triglycerides, for example, the commercial products Myritol® 318 or Myritol® 331 (BASF) with unbranched fatty acid residues and glyceryl triisostearin with branched fatty acid residues, are in principle also suitable as additional oils, but due to their less favorable residue behavior, less preferred. Such triglyceride oils should preferably be present only in a total amount of about 0 to about 1% by weight, particularly preferably about 0 to about 0.5% by weight, in each case based on the weight of the composition, without taking into account possibly existing propellant.

Preferred symmetrical, asymmetrical or cyclic esters of carbonic acid with fatty alcohols are selected from dicaprylyl carbonate (Cetiol® CC), di-n-octyl carbonate, di-n-dodecylcarbonate, di-(2-ethylhexyl) carbonate or the esters according to the teaching of DE 19756454 A.

Preferred $C_8$-$C_{16}$ isoparaffins are selected from isodecane, isoundecane, isododecane, isotridecane, isotetradecane, isopentadecane, and isohexadecane, and mixtures thereof. Preference is given to $C_{10}$-$C_{13}$ isoparaffin mixtures, in particular those having a vapor pressure at about 20° C. of about 10 to about 400 Pa, preferably about 13 to about 300 Pa. Preferred $C_{18}$-$C_{30}$ isoparaffins are selected from isoeicosane, polyisobutenes or polydecenes, which are available, for example, under the name Emery® 3004, 3006, 3010 or under the name Ethylflo® from Albemarle or Nexbase® 2004G from Nestle, and 1,3-di-(2-ethylhexyl) cyclohexane (available, for example, under the trade name Cetiol® S from BASF).

Preferred branched saturated or unsaturated fatty alcohols having about 6 to about 30 carbon atoms are selected from 2-hexyl decanol, octyl dodecanol (Eutanol® G) and 2-ethylhexyl alcohol.

Particularly preferred compositions as contemplated herein contain mixtures of at least two oils, wherein at least one volatile silicone oil, in a total amount of about 10 to about 40% by weight, preferably about 15 to about 35% by weight, particularly preferably about 20 to about 30% by weight, further at least one non-volatile oil in a total amount of about 10 to about 50% by weight, preferably about 20 to about 45% by weight, particularly preferably about 25 to about 40% by weight and optionally a non-volatile silicone oil, preferably polydimethylsiloxane in a total amount of 0 to about 20% by weight, preferably from about 3 to about 15% by weight, particularly preferably from about 6 to about 13% by weight, are present. In compositions extraordinarily preferred as contemplated herein, the oil composition is a mixture of decamethylcyclopentasiloxane as a volatile silicone oil, isopropyl myristate as a non-volatile oil, polydimethylsiloxane having a viscosity of about 5 cSt as a non-volatile silicone oil and additionally ethylhexyl palmitate, in each case based on the weight of the composition, without taking into account possibly existing propellant.

Fragrances and scents as contemplated herein do not belong to the oils d).

The definition of a fragrance in the context of the present application corresponds to the general expert definition as it can be found in the RÖMPP Chemie Lexikon, version of December 2007. Accordingly, a fragrance is a chemical compound having odor and/or taste that excites the receptors of the hair cell of the olfactory system (adequate stimulus). The necessary physical and chemical properties for this are a low molecular weight of at most about 300 g/mol, a high vapor pressure, minimal water and high lipid solubility and weak polarity and the presence of at least one osmophoric group in the molecule. In order to distinguish volatile, low molecular weight substances, which, usually and in the context of the present disclosure, are not regarded and used as a fragrance but rather primarily as a solvent, such as, for example, ethanol, propanol, isopropanol and acetone, from fragrances as contemplated herein, fragrances as contemplated herein have a molecular weight of about 74 to about 300 g/mol, contain at least one osmophoric group in the molecule and have an odor and/or taste, that is, they excite the receptors of the hair cells of the olfactory system. Examples of scent and fragrance compounds of the ester type are benzyl acetate, phenoxyethyl isobutyrate, p-tert-butylcyclohexyl acetate, linalyl acetate, dimethylbenzylcarbinylacetate (DMBCA), phenylethylacetate, benzylacetate, ethylmethylphenylglycinate, allylcyclohexylpropionate, styrallylpropionate, benzylsalicylate, cyclohexylsalicylate, floramate, melusate and jasmecyclate. Examples of scent and fragrance compounds of the ether type are benzyl ethyl ether and ambroxane, examples of scent and fragrance compounds of the aldehyde type are the linear alkanals having about 8 to about 18 carbon atoms, citral, citronellal, citronellyloxy-acetaldehyde, cyclamen aldehyde, lilial and bourgeonal, examples of scent and fragrance compounds of the ketone type are the ionones, alpha-isomethyl-ionone and methyl cedryl ketone, examples of scent and fragrance compounds of the alcohol type are anethole, citronellol, eugenol, geraniol, linalool, phenylethyl alcohol and terpineol, examples of scent and fragrance compounds of the terpene type are limonene and pinene. Examples of scent and fragrance compounds are pine, citrus, jasmine, patchouly, rose, ylang-ylang, muscatel sage oil, chamomile, clove oil, mint oil, cinnamon oil, lime blossom oil, juniper berry oil, vetiver oil, olibanum oil, galbanum oil, labdanum oil, orange blossom oil, neroli oil, orange peel oil and sandalwood oil, further the essential oils such as angelica root oil, aniseed oil, arnica blossom oil, basil oil, bay oil, bergamot oil, champacilla oil, silver fir oil, silver fir cone oil, elemi oil, eucalyptus oil, fennel oil, spruce needle oil, geranium oil, ginger grass oil, guaiac wood oil, gurdyal balm oil, helichrysum oil, ho oil, ginger oil, iris oil, cajeput oil, calamus oil, chamomile oil, camphor oil, kanga oil, cardamom oil, cassia oil, pine needle oil, copaiba balsam oil, coriander oil, spearmint oil, caraway oil, cumin oil, lavender oil, lemon grass oil, lime oil, tangerine oil, lemon balm oil, musk kernel oil, myrrh oil, clove oil, niaouli oil, orange oil, oregano oil, palmarosa oil, patchouli oil, Peru balsam oil, petit grain oil, pepper oil, peppermint oil, allspice oil, pine oil, rose oil, rosemary oil, sandalwood oil, celery oil, spik oil, star anise oil, turpentine oil, thuja oil, thyme oil, verbena oil, juniper berry oil, wormwood oil, wintergreen oil, hyssop oil, cinnamon oil, citronella oil, lemon oil and cypress oil. Further scent and fragrance compounds are ambrettolide, alpha-amylcinnamaldehyde, anethole, anisaldehyde, anisalcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerate, borneol, bornyl acetate, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, hepticarboxylic acid methyl ester, heptaldehyde, hydroquinone dimethyl ether, hydroxycinnamaldehyde, hydroxycinnamyl alcohol, indole, iron, isoeugenol, isoeugenol methyl ether, isosafrole, jasmon, camphor, carvacrol, carvone, p-cresol methyl ether, coumarin, p-methoxyacetophenone, methyl n-amyl ketone, methyl anthranilic acid methyl ester, p-methyl acetophenone, methyl chavikol, p-methyl quinoline, methylβnaphthyl ketone, methyl-n-nonyl acetaldehyde, methyl n-nonyl ketone, muscone, β-naphthol ethyl ether, β-naphthol methyl ether, nerol, nitrobenzene, n-nonyl aldehyde, nonyl alcohol, n-octyl aldehyde, p-oxy acetophenone, pentadecanolide, β-phenylethyl alcohol, phenylacetaldehyde dimethyacetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thyme, thymol, γ-undecalactone, vanillin, veratrum aldehyde, cinnamaldehyde, cinnamyl alcohol, cinnamic acid, cinnamic acid ethyl ester and cinnamic acid benzyl ester.

Further (more volatile) fragrances are alkyl isothiocyanates (alkyl mustard oils), butanedione, limonene, linalool, linalyl acetate and propionate, menthol, menthone, methyl-n-heptenone, phellandrene, phenylacetaldehyde, terpinyl acetate, citral and citronellal.

Preferably, mixtures of different fragrances are used, which together produce an attractive fragrance.

Suitable perfume oils may also contain natural perfume mixtures, such as those obtainable from plant or animal sources, for example, pine, citrus, jasmine, rose, lily or ylang-ylang oil. Essential oils of lower volatility, which are mostly used as aroma components, are also suitable as perfume oils, for example, sage oil, chamomile oil, lemon balm oil, mint oil, cinnamon oil, lime blossom oil, juniper berry oil, vetiver oil, oliban oil, galbanum oil, laudanum oil, clove oil, iso-eugenol, thyme oil, bergamot oil, geranium oil and rose oil.

Preferred compositions as contemplated herein are exemplified in that at least one scent is present in a total amount of from about 0.1 to about 15% by weight, preferably from about 0.5 to about 10% by weight, particularly preferably from about 1 to about 8% by weight, most preferably from about 2 to about 7% by weight, further extremely preferably from about 3 to about 6% by weight, each based on the total weight of the propellant-free composition.

Further preferred compositions as contemplated herein are exemplified by a content of at least one so-called "skin-cooling active substance". Skin-cooling active substances in the context of the present application are understood to mean active substances which, on application to the skin due to surface anesthetization and irritation of the cold-sensitive nerves in migraine and the like, generate a pleasant feeling of cold, even when the treated skin areas actually show normal or elevated temperature. As contemplated herein, skin-cooling active substances are regarded as those compounds which, like 1-menthol, stimulate the thermoreceptors in the skin and the mucous membranes in such a way that a cool sensory impression is created. In particular, the receptor CMR-1 ("cold and menthol-sensitive receptor"), which belongs to the family of TRP channels, is stimulated by the cooling substances, which produces a cold impression.

Preferred skin-cooling active substances are menthol, isopulegol and menthol derivatives, for example, menthyl lactate, menthylpyrrolidonecarboxylic acid, menthylmethyl ether, menthoxypropanediol, menthone-glycerol acetal (9-methyl-6-(1-methylethyl)-1,4-dioxaspiro(4.5)decane-2-methanol), monomenthyl succinate and 2-hydroxymethyl-3,5,5-trimethylcyclohexanol. Particularly preferred skin-cooling active substances are menthol, isopulegol, menthyl lactate, menthoxypropanediol and menthylpyrrolidonecarboxylic acid. Preferred compositions as contemplated herein contain at least one skin-cooling active substance in a total amount of from about 0.01 to about 1% by weight, preferably from about 0.02 to about 0.5% by weight and more preferably from about 0.05 to about 0.2% by weight, in each case based on the total weight of the (propellant-free) composition.

In a further embodiment preferred as contemplated herein, the compositions as contemplated herein contain about 0 to at most about 5% by weight of ethanol.

Furthermore, the compositions as contemplated herein may contain additional deodorant active substances. Antimicrobial, antibacterial or germ-inhibiting substances, antioxidants or odor adsorbents (e.g., zinc ricinoleate) can be used as deodorant active substances. Suitable antimicrobial, antibacterial or germ-inhibiting substances are in particular organohalogen compounds and halides, quaternary ammonium compounds, a range of plant extracts and zinc compounds. Preference is given to halogenated phenol derivatives, such as hexachlorophene or Irgasan DP 300 (triclosan, 2,4,4'-trichloro-2'-hydroxydiphenyl ether), 3,4,4'-trichlorocarbanilide, chlorhexidine (1,1'-hexamethylene-bis-[5-(4-chlorophenyl)]-biguanide), chlorhexidine gluconate, benzalkonium halides and cetylpyridinium chloride. Furthermore, sodium bicarbonate, sodium phenolsulfonate and zinc phenolsulfonate and, for example, the constituents of lime blossom oil can be used. Even less effective antimicrobial substances, which, however, have a specific effect against the gram-positive bacteria responsible for sweat decomposition can be used as deodorant active substances. Benzyl alcohol can also be used as a deodorant active substance. Further antibacterial deodorants are lantibiotics, glycoglycerolipids, sphingolipids (ceramides), sterols and other substances that inhibit bacterial adhesion to the skin, e.g., glycosidases, lipases, proteases, carbohydrates, di- and oligosaccharide fatty acid esters and alkylated monosaccharides and oligosaccharides. Preferred deodorant active substances are long-chain diols, for example 1,2-alkane ($C_5$-$C_{18}$) diols, glycerol mono ($C_8$-$C_{18}$) fatty acid esters or, more preferably, glycerol mono-($C_6$-$C_{16}$) alkyl ethers, in particular 2-ethylhexyl glycerol ethers, which are very well tolerated by skin and mucous membranes and are active against corynebacteria, and furthermore phenoxyethanol, phenoxyisopropanol (3-phenoxy-propan-2-ol), anisalcohol, 2-methyl-5-phenyl-pentane-1-ol, 1,1-dimethyl-3-phenyl-propan-1-ol, benzyl alcohol, 2-phenylethane-1-ol, 3-phenyl-propan-1-ol, 4-phenylbutan-1-ol, 5-phenylpentane-1-ol, 2-benzylheptan-1-ol, 2,2-dimethyl-3-phenylpropan-1-ol, 2,2-dimethyl-3-(3'-methylphenyl)-propan-1-ol, 2-ethyl-3-phenylpropan-1-ol, 2-ethyl-3-(3'-methylphenyl)-propan-1-ol, 3-(3'-chlorophenyl)-2-ethyl-propan-1-ol, 3-(2'-chlorophenyl)-2-ethyl-propan-1-ol, 3-(4'-chlorophenyl)-2-ethyl-propan-1-ol, 3-(3',4'-dichlorophenyl)-2-ethyl-propan-1-ol, 2-ethyl-3-(2'-methylphenyl)-propan-1-ol, 2-ethyl-3-(4'-methylphenyl)-propan-1-ol, 3-(3',4'-dimethylphenyl)-2-ethyl-propan-1-ol, 2-ethyl-3-(4'-methoxyphenyl)-propan-1-ol, 3-(3',4'-dimethoxyphenyl)-2-ethyl-propan-1-ol, 2-allyl-3-phenylpropan-1-ol and 2-n-pentyl-3-phenylpropan-1-ol.

Complex-forming substances can also support the deodorizing effect by stably complexing the oxidative catalytically active heavy metal ions (e.g., iron or copper). Suitable complexing agents are, for example, the salts of ethylenediaminetetraacetic acid or nitrilotriacetic acid and the salts of 1-hydroxyethane-1,1-diphosphonic acid. A further embodiment of the compositions as contemplated herein is exemplified in that at least one encapsulated active substance is present. The active substances which can be advantageously encapsulated are, in particular, deodorizing active substances, fragrances, perfume oils and/or skin-cooling active substances, but also other skin-care active substances, such as vitamins, antioxidants, etc.

Preferred capsule material are water-soluble polymers such as carboxymethylcellulose, methylcellulose, hydroxyethylcellulose or hydroxypropylmethylcellulose, carrageenans, alginates, maltodextrins, dextrins, vegetable gums, pectins, xanthans, polyvinyl acetate and polyvinyl alcohol, polyvinylpyrrolidine, polyamides, polyesters and homo- and copolymers of monomers selected from acrylic acid, methacrylic acid, maleic acid, fumaric acid, itaconic acid and the esters and the salts of these acids, and any mixtures of these polymers. Suitable capsule materials are also described, for example, in WO 2010/009977 A2.

In a further particularly preferred embodiment, the compositions as contemplated herein can contain both at least one antiperspirant active substance and at least one deodorant active substance. The preparation of the compositions as contemplated herein which are applied as a spray preferably depends on the requirements of the desired spray application.

The compositions as contemplated herein are present in the form of a suspension, that is, the antiperspirant active substance and optionally further insoluble constituents are suspended in a liquid or solid carrier. Liquid-disperse systems of this type, for example, as roll-ons or as a dispersion to be applied as a spray, should be shaken before use.

Preferred compositions as contemplated herein can be packaged, for example, in pump or squeeze dispensers, in particular in multi-chamber pump or squeeze dispensers. Such dispensers use air, in particular the ambient air, as a propellant or transport the composition as contemplated herein by pumping.

In a further preferred embodiment of the present disclosure, the composition is applied using a compressed or liquefied propellant. For this purpose, the composition as contemplated herein is packaged together with a propellant in a spray can. Propellant and composition as contemplated herein can be present as a mixture. However, it is also possible for the propellant and composition as contemplated herein to be present separately from one another, for example, in the case of so-called bag-in-can spray cans.

Unless specified otherwise, all amount specifications are based on the weight of the propellant-free composition.

The packaging in a multi-chamber dispenser offers special technical advantages. The multi-chamber dispenser can also be used so that one chamber is filled with the composition as contemplated herein, while another chamber contains the compressed propellant. Such a multi-chamber dispenser is, for example, a so-called bag-in-can packaging.

However, both chambers can also be joined together in such a way that the composition as contemplated herein is separated into two partial compositions which can be dispensed simultaneously from the packaging, for example, from separate openings or from a single opening.

Further preferred compositions as contemplated herein are exemplified in that they are packaged with at least one propellant in a suitable pressure container.

Propellants (propellant gases) preferred as contemplated herein are selected from propane, propene, n-butane, isobutane, isobutene, n-pentane, pentene, isopentane, isopentene, methane, ethane, dimethyl ether, nitrogen, air, oxygen, nitrous oxide, dichlorofluoromethane, chlorodifluoromethane, chlorofluoromethane, 1,1,2,2-tetrachloro-1-fluoroethane, 1,1,1,2-tetrachloro-2-fluoroethane, 1,2,2-trichloro-1,1-difluoroethane, 1,1,2-trichloro-1,2-difluoroethane, 1,1,1-trichloro-2,2-difluoroethane, 2,2-dichloro-1,1,1-trifluoroethane, 1,2-dichloro-1,1,2-trifluoroethane, 2-chloro-1,1,1,2-tetrafluoroethane, 1-chloro-1,1,2,2-tetrafluoroethane, 1,1,2-trichloro-2-fluoroethane, 1,2-dichloro-1,2-difluoroethane, 1,2-dichloro-1,1-difluoroethane, 1-chloro-1,2,2-trifluoroethane, 2-chloro-1,1,1-trifluoroethane, 1-chloro-1,1,2-trifluoroethane, 1,2-dichloro-1-fluoroethane, 1,1-dichloro-1-fluoroethane, 2-chloro-1,1-difluoroethane, 1-chloro-1,1-difluoroethane, 1-chloro-2-fluoroethane, 1-chloro-1-fluoroethane, 2-chloro-1,1-difluoroethene, 1,1,1,3-tetrafluoroethane, heptafluoro-n-propane, perfluoroethane, monochlorodifluoromethane, 1,1-difluoroethane, both individually and in combination.

Particularly preferred are propane, n-butane, isobutane and, most preferably, mixtures of these propellants. Further, also preferred are 1,1-difluoroethane, propane, n-butane, isobutane and mixtures of these propellants, in particular mixtures of 1,1-difluoroethane and n-butane.

Hydrophilic propellants, such as carbon dioxide, can also be advantageously used in the context of the present disclosure, when the fraction of hydrophilic gases is selected low and lipophilic propellant gas (e.g., propane/butane) is present in excess. Propane, n-butane, isobutane and mixtures of these propellants are particularly preferred. It has been found that the use of n-butane as sole propellant gas can be particularly preferred as contemplated herein.

The amount of propellant is preferably from about 10 to about 95% by weight, more preferably from about 30 to about 90% by weight and most preferably from about 60 to about 86% by weight, and still more preferably about 70, about 72, about 74, about 76, about 78, about 82, about 84 or about 85% by weight, each based on the total weight of the preparation including the composition as contemplated herein (suspension) and the propellant.

Vessels made of metal (aluminum, tinplate, tin), protected or non-splitting plastic or made of glass, which is coated with plastic outside, may be considered as a pressurized gas container, where in their selection, pressure and fracture resistance, corrosion resistance, easy fillability and aesthetic aspects, handiness, printability, etc. play a role. Special interior protective lacquers ensure corrosion resistance with respect to the suspension as contemplated herein. An inner protective lacquer preferred as contemplated herein is an epoxy phenolic lacquer, which is obtainable, among other things, under the name Hoba 7407 P. Particularly preferably, the valves used have an internally lacquered valve disk, wherein lacquer and valve material are compatible with each other. If aluminum valves are used, their valve disks can be coated inside, for example, with Micoflex lacquer. If tinplate valves are used as contemplated herein, their valve disks can be coated on the inside, for example, with PET (polyethylene terephthalate).

The cans are equipped with a suitable spray head. Depending on the spray head, discharge rates, based on fully filled cans, of about 0.1 g/s to about 2.0 g/s are possible.

Further, a subject of the present disclosure is a sprayable antiperspirant containing a composition as contemplated herein, exemplified in that the composition is present in an aerosol can with a compressed gaseous propellant.

A further subject of the present disclosure is a non-therapeutic, cosmetic method for reducing and/or regulating perspiration and/or body odor, in which a composition as contemplated herein is applied in an effective amount to the skin, preferably to the skin in the underarm region.

A further subject of the present disclosure is the use of rice starch and a hydrophobically modified clay mineral in suspensions of antiperspirant active substances in oils in substantially anhydrous antiperspirant compositions, preferably for improving the stability of the suspension, wherein the antiperspirant compositions are particularly preferred compositions as contemplated herein.

The present disclosure is further described by the following examples without being limited thereto.

EXAMPLES

The ingredients (see table) were mixed at 30° C. and homogenized to prepare the antiperspirant suspensions. Each 100 mL of the preparations were stored for 24 h at room temperature in stationary cylinders. The deposition of the clear oil phase indicates the sedimentation of the ACH particles (aluminum chlorhydroxide). Only the combination of rice starch with a hydrophobically modified clay mineral (Disteardimonium Hectorite (Bentone® 38 V CG)) gives the desired effect.

Table 1 shows four comparative formulations (V1), (V2), (V3) and (V4) and a formulation (E) as contemplated herein, wherein the present disclosure is not limited to these. Table 2 shows three inventive compositions (E1), (E2) and (E3), which are filled in a weight ratio of 3:17 with the propellant propane/butane (15/85) in aerosol cans.

TABLE 1

Four comparative formulations (V1), (V2), (V3) and (V4) and a formulation (E) as contemplated herein, and the evaluation of the sedimentation of the individual formulations after 24 h

|  | V1 % by weight | V2 % by weight | V3 % by weight | V4 % by weight | E % by weight |
|---|---|---|---|---|---|
| Octenylsuccinate of a hydrolyzed corn starch | — | 0.5 | — | — | — |
| Rice starch | — | — | 0.5 | — | 0.5 |
| Disteardimonium hectorite | — | 2.5 | — | 2.5 | 2.5 |
| Cyclopentasiloxane | 29.5 | 26.5 | 29.0 | 28.0 | 26.5 |
| Isopropyl myristate | 30.0 | 30.0 | 30.0 | 30.0 | 30.0 |
| Ethylhexyl palmitate | 6.0 | 6.0 | 6.0 | 6.0 | 6.0 |
| Dimethicone 5 cSt | 10.0 | 10.0 | 10.0 | 10.0 | 10.0 |
| Propylene carbonate | 1.0 | 1.0 | 1.0 | 1.0 | 1.0 |
| Aluminum chlorhydrate (spherical particles) | 23.5 | 23.5 | 23.5 | 23.5 | 23.5 |
| Sedimentation after 24 h at room temperature | Strong (6 cm clear oil) | Strong (5 cm clear oil) | Moderate (3 cm clear oil) | Weak (2 cm clear oil) | none |

TABLE 2

Three compositions as contemplated herein (E1), (E2) and (E3), which are filled in a weight ratio of 3:17 with the propellant propane/butane (15/85) in aerosol cans

|  | E1 % by weight | E2 % by weight | E3 % by weight |
|---|---|---|---|
| Cyclopentasiloxane (Xiameter 0245 fluid) | 21.5 | 21.1 | 21.7 |
| Isopropyl palmitate (BASF) | 30.0 | 30.0 | 30.0 |
| Ethyl hexyl palmitate (Cegesoft C24, BASF) | 6.0 | 6.0 | 6.0 |
| Rice starch (rice starch D.S.A. 7, Agrana AG) | 0.5 | 0.9 | 0.3 |
| Dimethicone (Xiameter PMX-200 Fluid 5CS) | 10.0 | 10.0 | 10.0 |
| Disteardimonium hectorite | 2.5 | 2.5 | 2.5 |
| Propylene carbonate | 1.0 | 1.0 | 1.0 |
| Aluminum chlorhydrate (AACH 7172, SummitRheheis) | 23.5 | 23.5 | 23.5 |
| Perfume | 5.0 | 5.0 | 5.0 |

The invention claimed is:

1. An antiperspirant composition for personal body care comprising
   a) at least one antiperspirant active substance present in the form of spherical particles, in suspended, undissolved form, and selected from aluminum salts, in a total amount of about 23 to about 27% by weight,
   b) about 0.4 to about 1% by weight of rice starch,
   c) about 1.5 to about 3.5% by weight of disteardimonium hectorite,
   d) at least one oil in a total amount of about 60 to about 75% by weight, wherein the at least one oil comprises at least one volatile silicone oil present in a total amount of from about 20 to about 30% by weight, wherein the at least one volatile silicone oil is decamethylcyclopentasiloxane, wherein the at least one oil further comprises at least two non-volatile oils present in a total amount of from about 25 to about 40% by weight, wherein the at least two non-volatile oils are isopropyl myristate and 2-ethylhexyl palmitate, and wherein the at least one oil comprises at least one non-volatile silicone oil present in a total amount of about 6 to about 13% by weight, and wherein the at least one non-volatile silicone oil is polydimethylsiloxane having a viscosity of about 5 cSt,
   wherein all weight % specifications are based on the weight of the composition, without taking into account any propellants which may be present.

2. The composition according to claim 1, wherein the at least one antiperspirant active substance (a) is aluminum chlorohydrate.

3. The composition according to claim 1, wherein the rice starch is present as a powder treated with cationic surfactants, wherein the fraction of cationic surfactants is from about 0.01 to about 0.3% by weight, based on the weight of the rice starch.

4. The composition according to claim 1, wherein from about 70 to about 95% by weight of the spherical particles have a size above 10 μm, from about 80 to about 100% by weight of the spherical particles have a size of up to about 75 μm and from about 90 to about 100% by weight of the spherical particles have a size up to about 125 μm, each based on the weight of the antiperspirant active substance.

5. The composition according to claim 1, further comprising at least one perfume present in a total amount of from about 0.1 to about 15% by weight, based on the total weight of the propellant-free composition.

6. The composition according to claim 1 wherein a ratio of the rice starch to the hydrophobically modified clay mineral is from about 3.1 to about 8.3.

* * * * *